United States Patent [19]

Bitterly

[11] Patent Number: 4,867,344

[45] Date of Patent: Sep. 19, 1989

[54] PRESSURIZED DISPENSER

[75] Inventor: Jack G. Bitterly, Woodland Hills, Calif.

[73] Assignee: Thermacor Technology, Inc., Newbury Park, Calif.

[21] Appl. No.: 64,870

[22] Filed: Jun. 19, 1987

Related U.S. Application Data

[63] Continuation-in-part of Ser. No. 673,509, Nov. 19, 1988, Pat. No. 4,756,310, and a continuation-in-part of Ser. No. 709,093, Mar. 7, 1985.

[51] Int. Cl.$^4$ .......................... B65D 35/28; B67D 5/42
[52] U.S. Cl. ......................................... 222/94; 222/95; 222/105; 222/131; 222/386.5; 222/389; 222/399; 239/323
[58] Field of Search ................... 222/1, 55, 61, 94, 95, 222/105, 131, 386.5, 387, 389, 399, 527, 573, 183; 239/323

[56] References Cited

U.S. PATENT DOCUMENTS

| | | | |
|---|---|---|---|
| 270,810 | 1/1883 | Kaye | 222/573 |
| 2,815,152 | 12/1957 | Mills | 222/386.5 |
| 3,245,582 | 4/1966 | Roth et al. | 222/386.5 X |
| 3,417,901 | 12/1968 | Sands | 222/386.5 X |
| 3,640,277 | 2/1972 | Adelberg | 222/386.5 X |
| 3,896,970 | 7/1975 | Laauwe | 222/94 |
| 3,992,003 | 11/1976 | Visceglia et al. | 222/94 |
| 4,159,790 | 7/1979 | Bailey | 222/386.5 X |
| 4,202,470 | 5/1980 | Fujii | 222/386.5 X |
| 4,430,078 | 2/1984 | Sprague | 222/94 X |
| 4,440,319 | 4/1984 | Nitchman et al. | 222/183 X |
| 4,527,715 | 7/1985 | Rosenbaum | 222/55 X |

Primary Examiner—Joseph J. Rolla
Assistant Examiner—Steven M. Reiss
Attorney, Agent, or Firm—Poms, Smith, Lande, & Rose

[57] ABSTRACT

A container for dispensing a refrigerant as a liquid under pressure includes a vessel for holding the refrigerant. The bladder in the vessel has a relatively small amount of a liquid having a higher vapor pressure greater than the vapor pressure of the refrigerant. The bladded has flexible walls so that the vaporized pressurizing fluid expands the bladder walls to pressurize the refrigerant in the first container. The pressure maintains the refrigerant as a liquid under pressure as refrigerant is dispensed from the vessel. A channel member may also be provided within the vessel for channeling liquid refrigerant between regions of the vessel if the bladder or the collapsing vessel blocks a portion of the inside of the vessel. Alternatively, the bladder surrounds the vessel. The bladder and vessel are within an outer container. As the bladder expands, it collapses the walls of the vessel when refrigerant is dispensed from the first container.

5 Claims, 3 Drawing Sheets

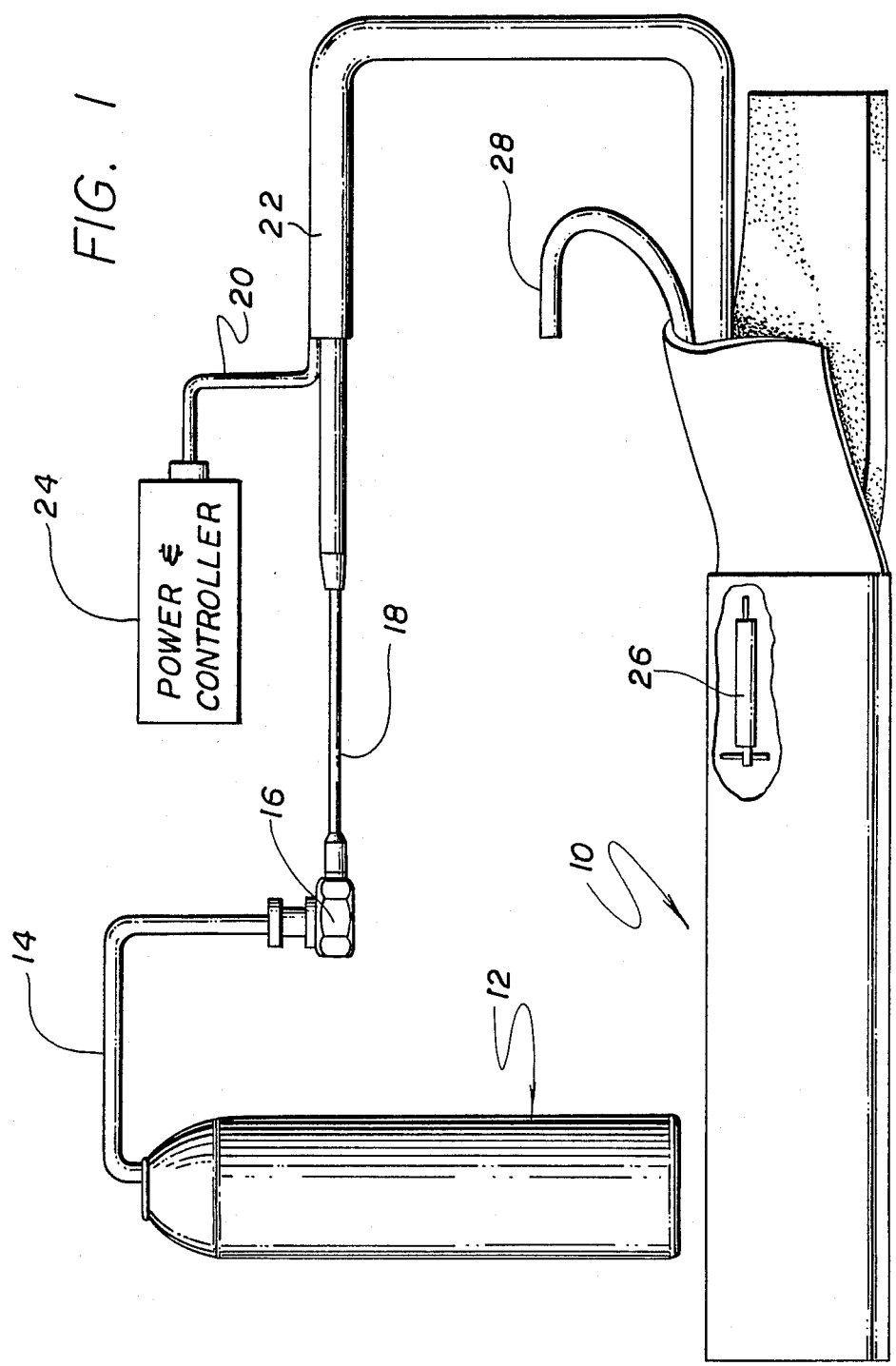

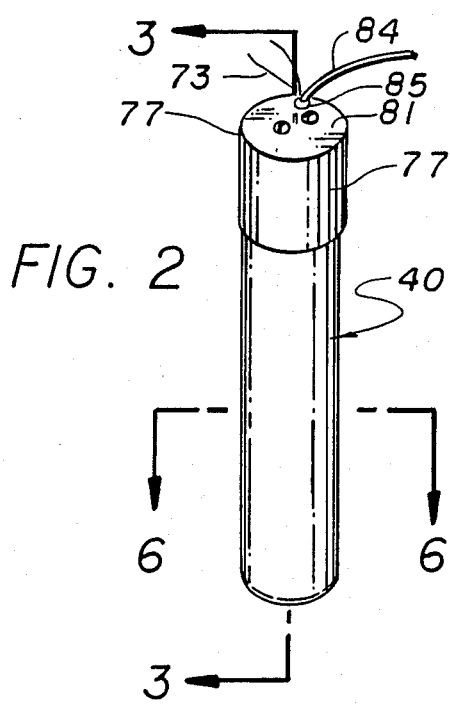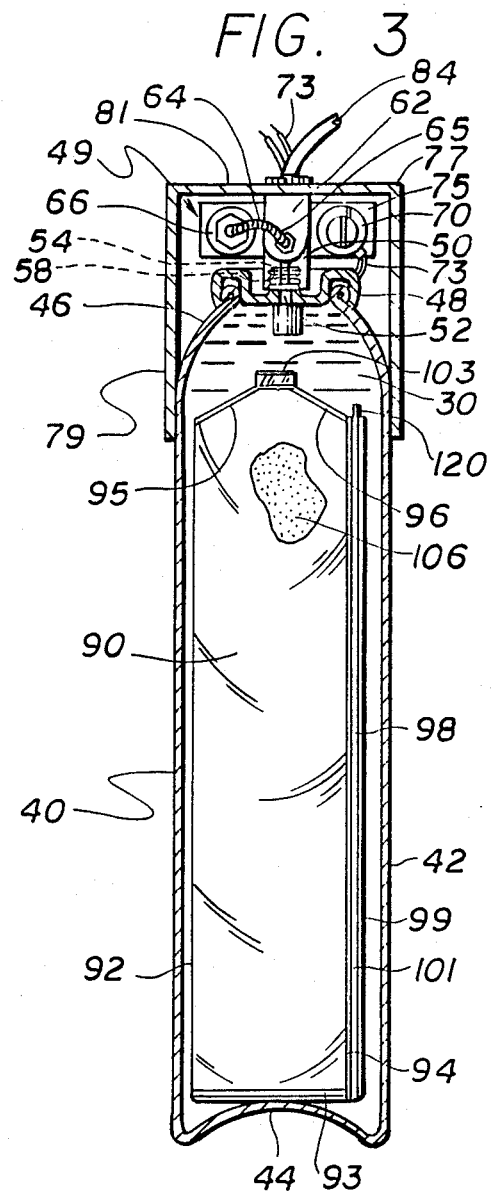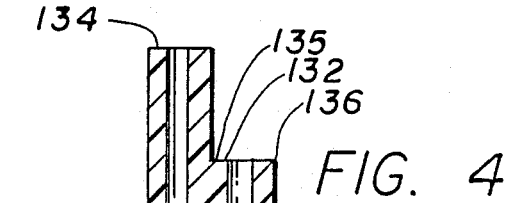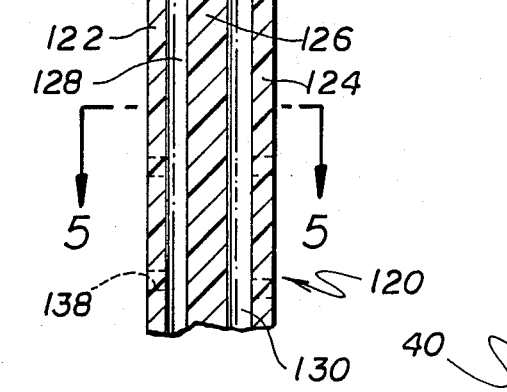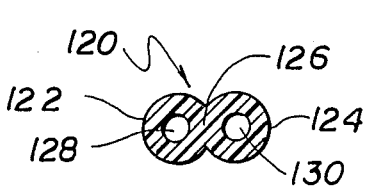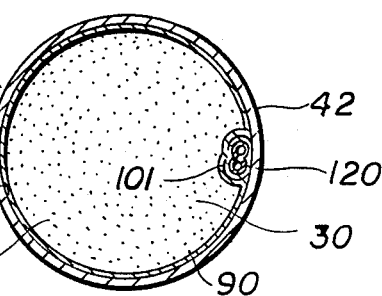

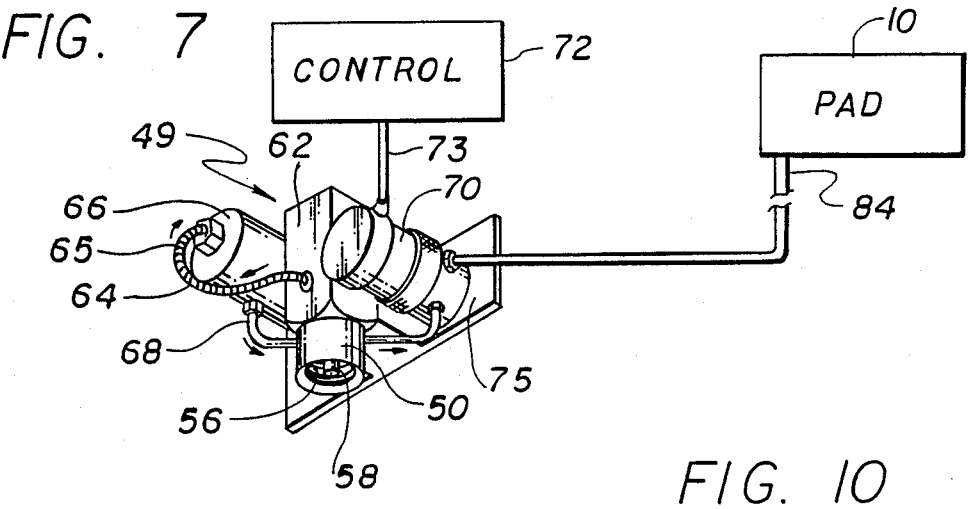
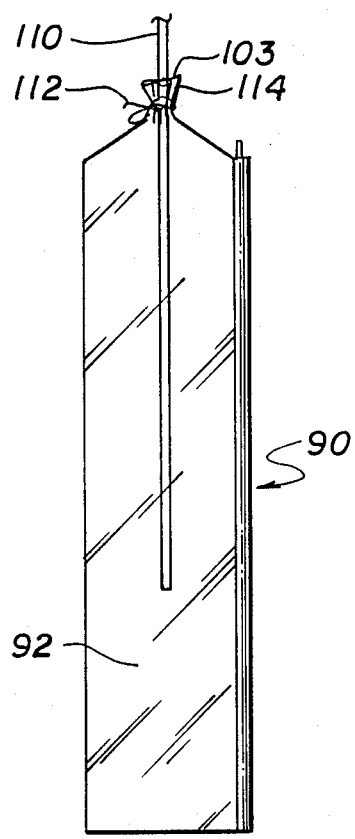
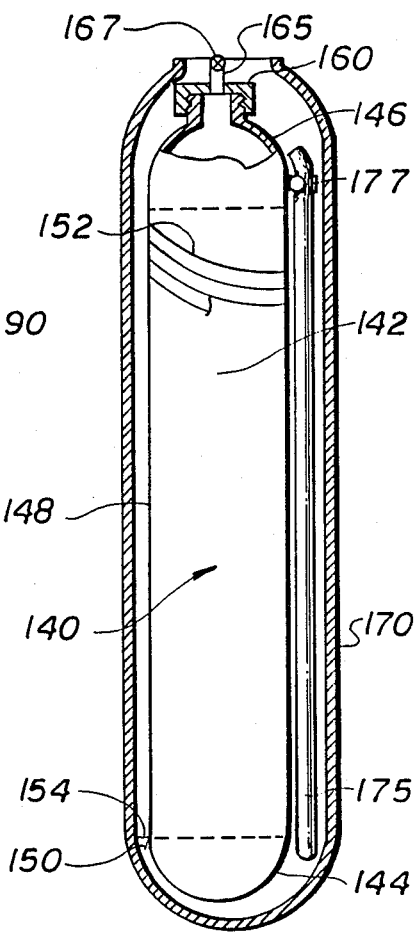

PRESSURIZED DISPENSER

RELATED APPLICATIONS

This application is a continuation-in-part of applicant's pending applications Ser. No. 673,509, filed November 19, 1984, entitled "System for Cooling an Area of the Surface of an Object," now Pat. No. 4,756,310 (July 12, 1988)and Ser. No. 709,093, filed March 7, 1985, entitled "Localized Cooling Apparatus."

BACKGROUND OF THE INVENTION

1. Field of Invention:

This invention relates to a relatively low cost container for dispensing a working fluid under pressure and a method for dispensing working fluid under pressure.

2. Prior Art:

Applicant's earlier pending application Ser. No. 709,093 discloses a fabric that can be used to cool areas of the body. The system injects into the fabric a liquid that boils at a relatively low temperature. Body heat causes the liquid to change phase (boil), which cools the skin. This same method is the basis of some of applicant's other patent applications and in his earlier U.S. Pat. Nos. 3,479,838 (1969) and 4,569,355 (1986).

In applicant's patents and pending application Ser. No. 673,509, the low temperature boiling has as its primary function to cool a small disk, which is placed against the skin. By cooling the small area of the skin and allowing blood flow to warm the skin after the device stops cooling the skin, one can measure peripheral blood flow. As a blood flow monitor, portability is usually not a major concern. Portability is more important for the more general cooling fabric if one does not want to be tied to relatively heavy, complex tanks.

Applicant's earlier application Ser. No. 673,509 discloses a vessel that holds two liquids, a refrigerant and a pressurizing fluid. A movable piston divides the two fluids. The pressurizing fluid has a vapor pressure higher than the pressure of the refrigerant so that the pressurizing fluid, which is part liquid and mostly gas, urges the piston against the refrigerant. As the refrigerant volume decreases, a portion of the pressurizing fluid changes phase from a liquid to a gas to replace the volume of the refrigerant dispensed. This replacement maintains a constant pressure, which is the vapor pressure of the pressurizing fluid when the refrigerant is dispensed. The pressure from the pressurizing fluid exerts force on the piston to maintain the refrigerant above its vapor pressure so that it remains in the liquid phase in the volume allocated to its storage. As the previous applications indicate, it is important to maintain the refrigerant in its liquid state so that it can only boil when it is injected into the cooling fabric or heat exchange disk. Therefore, it retains its value as a coolant in the liquid state until it reaches the precise location where cooling is desired. The increased pressure also allows the refrigerant to be transported from its storage tank for use at high pressures. Because the refrigerant is at higher than its normal vapor pressure, it can flow faster than lower pressure fluids would flow in a tube of a given cross-section. Also, liquid volume controls are more precise than gas controls. It is important to inject a controlled amount of refrigerant to regulate the rate of cooling.

SUMMARY OF THE INVENTION

It is an object of the present invention to disclose and provide a lightweight vessel for dispensing working fluid under sufficient pressure that it remains as a liquid. The complex vessel with a piston of the previously mentioned application is relatively costly to manufacture. It is an object of the present invention to disclose a container that is relatively inexpensive, which can be discarded after use.

The previously discussed vessel with a piston is designed to work primarily in an upright orientation. A portable system may have to work in several different environments. For example, if the cooling fabric is part of a fireman's clothing or helmet, the tank for supplying the refrigerant to the cooling fabric would probably be mounted on the fireman's back or belt. The tank only is in an upright position if the fireman is standing. If he crawls through an opening or bends over, the tank inverts or is in some other position such that the bottom of the refrigerant tank could be oriented above the top of the tank. It is an object of the present invention to disclose and provide a pressurized tank that could be used in all orientations and deliver all of the coolant in the liquid phase from the tank. Although the tank is used in an embodiment in which it is delivering refrigerant liquid to a cooling garment, the system also could be used to insure that only liquid from an aerosol container is delivered under pressure regardless of the orientation of the container.

To minimize the cost of filled tanks, the vessel must be relatively inexpensive to fill. If the cost of the fluids is fixed, it is important, therefore, to minimize the labor expense in having the tanks properly filled and to minimize the lost fluid in the filling procedure. It is also important that all of the refrigerant in the tank is dispensed. The vessel itself should not block dispensing of any refrigerant. Minimizing labor and saving refrigerant are other objects of this invention.

The pressurized dispenser of the present invention includes a vessel which can be closed to hold pressurized refrigerant inside. In one embodiment, a bladder with flexible walls is placed inside the vessel. There may be a connection into the bladder through the vessel. The bladder contains a relatively small amount of a second fluid having a vapor pressure higher than the refrigerant. When the entire vessel is closed, some of the pressurizing liquid vaporized inside the bladder, which causes the bladder to expand. The expansion decreases the remaining volume within the vessel to pressurize the refrigerant to the vapor pressure of the pressurizing flujd. This pressurizes the refrigerant to maintain it in its liquid state. When the vessel dispenses refrigerant, the volume of that fluid decreases. More pressurizing fluid in the bladder can vaporize, which causes the bladder to expand. The pressurizing fluid maintains the refrigerant as all liquid under constant pressure at a given temperature. As long as there is some liquid within the bladder, the fluid in the bladder remains in equilibrium at a pressure above the vapor pressure of the refrigerant and retains the refrigerant in its liquid state.

In another embodiment, a relatively flexible vessel is placed within a sleeve that does not expand. The bladder is placed between the vessel and the sleeve. The vessel is filled with liquid refrigerant, and the bladder receives sufficient pressurizing fluid. The expansion of the bladder pushes inward on the walls of the vessel, which decreases the volume and pressurizes the refrigerant within the vessel. As refrigerant is dispensed from the vessel, more pressurizing fluid vaporizes causing the bladder to expand, which maintains the refrigerant under pressure and as a liquid.

A bypass line is provided within the vessel between the inside wall and the bladder and extends substantially the entire length of the vessel. The line, which may be a thin wall plastic or metal tube carries refrigerant to the discharge end of the tank from the other end to ensure that the expanded bladder or the collapse of a portion of the vessel does not block remaining refrigerant from passing to the discharge end of the vessel. Proper sizing of the bladder and design of the bypass line insures that almost all of the refrigerant in the vessel can be ejected when the container is in any orientation.

BRIEF DESCRIPTION OF THE DRAWINGS

FIG. 1 is a schematic view of the cooling system that utilizes the vessel of the present invention.

FIG. 2 is a perspective view of the vessel and an associated cover utilized in one embodiment of the present invention.

FIG. 3 is an side sectional view of the vessel taken through plane 3—3 of FIG. 2.

FIG. 4 is a sectional view of a double tube used to conduct refrigerant from the bottom to the top of the vessel.

FIG. 5 is a sectional view of the double tube taken through plane 5—5 of FIG. 4.

FIG. 6 is a top sectional view of the vessel taken through plane 6—6 in FIG. 2.

FIG. 7 is a perspective view of the controller used with the vessel of the present invention.

FIG. 8 is a front elevation of the bladder used in the vessel of the present invention.

FIG. 9 is a perspective view showing insertion of the bladder into the vessel of the present invention.

FIG. 10 is a sectional view of a second embodiment of the vessel of of the present invention.

DETAILED DESCRIPTION OF THE PREFERRED EMBODIMENT

One of the main uses of the present invention is to supply working fluid, a refrigerant, to the cooling fabric or pad described in applicant's earlier patent applications. Pad 10 (FIG. 1) has within it means for dispensing refrigerant in close proximity to the skin so that body heat causes the refrigerant to boil. The cooling pad is described in applicant's earlier application Ser. No. 709,093. The change of phase of the refrigerant removes heat from the body and cools the skin. Coolant supply or vessel 12 is the source of refrigerant of cooling pad 10. The several embodiments of vessel 12 are the subject of this application.

Working fluid is dispensed through outlet tube 14 (only displayed schematically in FIG. 1) through connector 16 and through inlet line or tube 18. The inlet tube is bundled with electrical wiring 20 through a protective sheath 22. Wires 20 are connected to a battery power souce and controller unit 24. The controller operates a solenoid valve 26 or other valve system. Valve 26 is shown in FIG. 1 only to indicate its approximate position. The valve may be mounted within cooling pad 10 or may be mounted near the pad. The pad may be one of many pads mounted in a more general cooling garment, and a single valve 26 may dispense working fluid to more than one pad. In the exemplary embodiment, valve 26 is at the end of inlet line 18, and is controlled electrically from controller 24. After the liquid refrigerant boils, the vapor leaves the pad(s) through exhaust tube 28, which may be connected to a recycling system.

Outlet tube 14 from vessel 12 and tube 18 from pad 10 attach together at connector 16. The tubes can be attached and removed from connector 16 so that vessel 12 or pad 10 can be removed from the rest of the system. Connector 16 may be located in different positions. It may be mounted on fittings directly on vessel 12 as explained in the more detailed discussions of the exemplary embodiments of the vessels. Outlet 14 can also be used to fill or refill vessel 12. In the exemplary embodiment, the vessel is disposable, and tube 14 is not used to fill the vessel.

One embodiment of the vessel of the present invention is shown in FIGS. 2 and 3. The vessel is a metal can 40, which is in the shape of a standard aerosol can. Such cans are marketed in different sizes and with different pressure ratings. The correct vessel is chosen for the particular task and operating environment needed. Vessel 40 has a cylindrical side wall 42 and a curved bottom wall 44. A cap 48 is crimped to neck 46 and closes the top of vessel 40 after the tank is filled.

As explained in greater detail below, the present invention is designed to maintain working fluid 30 (FIG. 3) as a liquid. Applicant's earlier applications disclose the use of Freon$_{114}$, a registered trademark for a fluorocarbon fluid having desired vaporization characteristics. The present invention preferably uses Freon$_{114}$ as its refrigerant. Freon$_{114}$ has a boiling point of 39° F. (4° C.) and a vapor pressure of 16 psi (392 kPa).

Cap 48 has a central opening 52 (FIG. 3). As is common, the opening is closed by a valve, which opens when a dispenser member is inserted into the opening. Dispensing means are provided in the present invention for dispensing the refrigerant fluid 30 from vessel 40. In the examplary embodiment, the dispensing means comprises a dispensing fitting 50 (FIGS. 3 and 7). Fitting 50 has internal threads 56 which mate with external threads 54 around opening 52 on cap 48. A short pin 58 (FIGS. 3 and 7) extends into opening 52 when fitting 50 is threaded onto threads 54. The parts are designed so that the valve, which closes opening 52, does not allow pressurized fluid 30 to pass until pin 58 is fully extended into opening 52. The length of pin 58 is such that valve member 52 is opened only when fitting 50 is fully seated on threads 54. An O-ring (not shown) may be provided at the top of the inside of fitting 50 to seal the space between the inside of fitting 50 and the top of outer threaded member 54. An 3-ring also provides resistance to rotation of fitting 50 relative to the outer threaded member 54 so that one can feel the contact of the O-ring and that some further rotation is necessary for full engagement.

Liquid refrigerant 30 in fitting 50 flows through a dict (not shown) into manifold 62 (FIGS. 3 and 7). A short tube 64 carried the refrigerant from manifold 62 to pressure regulator 66. Variations in ambient temperature affect the refrigerant pressure within vessel 40, but it is advantageous to dispense liquid through valve 26 in cooling pak 10 at constant pressure. An increase in ambient temperature from 70° F. (20° C.) to 140° F. (60° C.) increases the internal pressure more than 10%.

In view of the potentially high pressure in line 64, the line passes through a helical metal winding 65, which protects tube 64 from rupturing. Metal is used in the exemplary embodiment, but any high tensile strength material that can be wound around tube 64 is acceptable.

The refrigerant flows at constant pressure from pressure regulator 66 through tube 68 to control valve 70. The control valve functions as an on/off control for the refrigerant. Valve 70 may be manually controlled. Manual control is especially appropriate if the user can reach the valve while the system is in use. Remote control is also possible in which a remote switch from control panel 72 acting through electrical wiring 73 (FIGS. 2, 3 and 7) opens and closes valve 70.

Fitting 50, pressure regulator 66 and valve 70 all mount on plate 75 (FIGS. 3 and 7). The plate and manifold 62 attach to vessel cover 77 (FIGS. 2 and 3). THe vessel cover is cylindrical in shape, and the inside diameter of the depending cylindrical wall 79 is slightly greater than the outside diameter of cylindrical wall 42 of vessel 40 (FIG. 3) to provide a relatively snug fit.

Openings are provided in top wall 81 of cover 77. In one embodiment, an outlet line 84 extends from a fitting (not shown) on valve 70, through a rubber washer 85 in top wall 81 and out of the cover (FIG. 2). Line 84 (FIGS. 2 and 3) is the equivalent to output line 14 (FIG. 1). Additional openings may be provided in cover 77 for various other parts. For example, a manual control for valve 70 may be mounted through the cover. Rather than having tube 84 extend through the cover to a fitting on the valve under the cover, the fitting for the tube could extend from the top of the cover, and the tube could be connected there directly.

A thin foam plastic insert (not shown) may be provided to protect the tubes connecting manifole 62, regulator 66 and valve 70, especially when cover 77 is removed from vessel 40.

The vessel of the present invention also includes a second container for holding a second fluid. The second fluid has a vapor pressure greater that the vapor pressure of refrigerant 30 in vessel 40. The second container has at least one flexible wall for acting on and pressurizing refrigerant 30. In one exemplary embodiment, the second container is a plastic bladder of sheet urethane or high tensile strength polyester. The diameter of the bladder is approximately equal to the diameter of cylindrical wall 42 (FIG. 6). The bladder may be formed in many ways, but in the exemplary embodiment, a single sheet of plastic is folded over itself at fold 92 (FIG. 3) and edges 93, 94, 95 and 96 are haled together. The edges could also be attached using an adhesive. Two short flaps (only one, flap 98 is visible in FIG. 3) extend beyond heat seal 94. The edge of the flaps are then hheat sealed together at 99. As a result, a narrow channel or sleeve 101 (FIGS. 3 and 6) is created. The purpose of this channel is discussed below. A small edge 103 at the top (FIG. 3) of the bladder is purposely not heat sealed initially.

The purpose of second container or bladder 90 is to contain the second fulid, which is also called the pressurizing fluid. The pressurizing fluid has a vapor prossure greater than the vapor pressure of the refrigerant. In the exemplary embodiment, the pressurizing fluid is a mixture of Freon$_{114}$ and Freon$_{12}$. The vapor pressure of the mixture changes as a function of the percentages of the two fluids. A 50% Freon$_{12}$ - 50% Freon$_{114}$ mixture has a vapor pressure of approximately 51.7 psi (358 kPa) at standard conditions. Increasing the percentage of Freon$_{12}$ raises the vapor pressure of the pressurizing fluid in the container. At 100% Freon$_{12}$, the vapor pressure is about 78.4 psi (541 kPa).

Pressurizing fluid 106 (FIG. 3) vaporizes within bladder 90 until the pressure within the bladder is equal to the vapor pressure of the vaporizing fluid. In a filling procedure discussed below, refrigerant liquid 30 almost fills vessel 90 except for the space occupied by bladder 90. A small amount of refrigerant 30 also vaporizes to fill any space not occupied by the refrigerant and bladder. Because the vapor pressure of the pressurizing fluid is greater than the vapor pressure of the refrigerant, the pressurizing fluid continues to vaporize and exerts pressure on the refrigerant. The gas phase of the refrigerant condenses and compresses. Both fluids are at the same 52 psi pressure, the vapor pressure of the vaporizing fluid. The refrigerant in vessel 40 remains a liquid because it is at a pressure much above its vapor pressure. It also remains a liquid even if the pressure drops somewhat from flowing through long tubes to the cooling apparatus or otherwise. The bladder continues to expand until there is no Freon refrigerant gas 30 in vessel 40. The bladder can continue to expand as long as there is some liquid pressurizing fluid 106 to continue to vaporize within bladder 90.

Bladder 90 and vessel 40 are filled in the following fashion. After bladder 90 is formed, a short fill tube 110 (FIG. 8) is inserted through opening 103 into bladdeer 90. A short length of string 112 is tied around neck 114 of bladder 90 and tube 110. String 112 is designed to close temporatily top 103 of bladder 90.

The bladder is then evacuated by connecting the outer end of tube 110 to a vacuum pump. The bladder tends to roll into the configuration shown in FIG. 9. Tube 110 is then connected to sources of liquid Freon$_{12}$ and Froeon$_{114}$ and both fluids are added in proper proportions. Preferably, the liquid Freon is stored at very cold temperatures (e.g. −40° F. to −90° F. (−40° C. to −60° C.)), which is substantially below the 0° F. (−18° C.) boiling point to Freon$_{12}$, to prevent its rapid vaporization. The amount of the pressurizing liquid added to the bladder depends on the dimensions of the vessel 40. The volume of pressurizing fluid should be such that if all but a very small amount of the fluid vaporizes and expands bladder 90, the full bladder would occupy the entire inside volume of vessel 40. Tube 110 is then removed from bladder 90, and neck 114 is then heat sealed so that all edges of the bladder are now closed. Sealed, filled bladders are stored at very low temperature to decrease greatly the vapor pressure of the pressurizing fluid so that little of the fluid vaporizes.

As an alternative, one or more valved tubes may extend through cap 48 for filling bladder 90 and/or vessel 40. Bladder 90 normally could be inserted into container 40 in its empty, evacuated condition and then filled through such a tube.

Vessels 40 are precooled and held in a cold box. They are then filled through neck 46 to a predetermined level iwth precooled working fluid, Freon$_{114}$. The Freon displaces the air in the container. The temperature to which the Freon$_{114}$ is pre-cooled depends on manufacturing conditions. If the fluid is allowed to warm for a relatively long time without being in a sealed container or if the filing takes place in a very warm environment, the Freon should be pre-cooled to very cold temperatures even below −50° F. (−46° C.). If filing takes place quickly in a refrigerated environment below the 36° F. (2° C.) boiling point of the fluid, the fluid does not have to be cooled as much. The level of Freon$_{114}$ in vessel 40 varies based on the size of the vessel and of the bladder. Bladder 90 remains, at least partially, in its rolled up state. It is then inserted into vessel 40 as FIG. 9 shows. The bladder may be inserted into a vessel without refrigerant, and the refrigerant may be added later. It is desirable that even after bladder 90 is inserted into vessel 40 that some space remain without liquid refrigerant. Cap 48 is then sealed on neck 46 of vessel 40 so that the entire vessel is sealed.

The sealed vessel is then removed from the cold box in which filling took place. As the vessel and the associated fluids warm, pressurizing fluid 106 vaporizes so that bladder 90 expands against liquid refrigerant 30. The gaseous refrigerant, which occupied th einitial space left because the vessel was not fully filled, condenses as the pressurizing fluid vaporizes. Newly filled containers have some space occupied by gas (in this case, gaseous pressurizing fluid 106) to compensate for temperature changes. The internal pressure may exceed the pressure rating of vessel 40 if a container that is filled entirely with incompressable liquid at a very low temperature is sealed and then subjected to a very high ambient temperature (e.g. 140° F. (60° C.)). Gas in the vessel or bladder is cmpressible to absorb some of the pressure forces. After filling, vessels 40 are stored at room temperature.

When refrigerant is needed in cooling patch 10 (FIG. 1), vessel 40 is mated with the various dispenser parts located in cover 77. As liquid flows to cooling pad 10, some of the pressurizing liquid 106 in bladder 90 vaporizes to maintain an elevated pressure above normal vapor pressure on refrigerant 30.

Bladder 56 may expand unevenly and may block the flow of refrigerant fluid from the bottom to the top dispensing end of vessel 40. Channeling means (FIGS. 3, 4, 5 and 6) are provide for channeling refrigerant fluid between parts of the vessel when the bladder expands against the inside wall of the vessel. In the exemplary embodiment, the channeling means is a plastic member 120, which forms one or more channels extending longitudinally between the top and bottom of the vessel. The channel member mey be generally straight or it may curve slightly.

One example of a channel member is shown in FIG. 4 for use in the FIG. 3 embodiment. Channel member 120 is similar to a short beverage stirrer. The outer walls 122 and 124 and the inner web 126 surround two channels, 128 and 130 (FIGS. 4 and 5). Wall 124 and part of web 126 are cut sharply to form shoulder 132. The plastic surrounding channel 128 extends beyond shoulder 132. This design created three sharp corners 134, 135 and 136 to prevent a part of bladder 90 from covering the ends of both channels 128 and 130. Openings 138 (FIG. 4) can extend through walls 122 or 124 to provide additional access to channels 128 and 130. The channel member conducts fluid from the bottom to the top, dispensing end of vessel 40.

The various accommodations such as two channels 128 and 130, shoulder 132, sharp corners 134, 135 and 136 and the side openings 138 are desirable in a system where the position of the bladder relative to the channel member is not well controlled. The FIG. 3 embodiment controls the position of the channel member relative to the bladder. When bladder 9/ is constructed, the spaced heat seal edges 94 and 99 (FIG. 3) create a sleeve 101 that receives a separate channel membere such as member 120. A separate, harder channel member such as member 120 is desirable within sleeve 101 because the material that forms the bladder is too soft to ensure that space 101 will not collapse in places.

In place of channel member 120, means may be provided for keeping the walls of sleeve 101 spaced apart enough so that fluid can flow through the sleeve. Sleeve 101 may also have holes to allow fluid to flow from the sides into the sleeve or the channel member. Channel member 120 also may be formed with short curved sections (not shown) at either end. The curvature is designed to conform to any curves inside vessel 40. A srefrigerant is needed and flows from vessel 40, bladder 90 expands until the outside wall 92 of bladder 90 contacts the inside of cylindrical wall 42 of vessel 40 (FIG. 6). Any liquid refrigerant trapped at the bottom (FIG. 3) end of the first container flows through channel member 101 from the bottom end to the top end (FIG. 3) where it can flow through fitting 52 and into outlet line 14 (FIG. 1).

One can vary the degree to which the expanded bladder 90 conforms to the inside of vesel 40. As long as the plastic material that forms the bladder can stretch, the bladder can conform to the inside shape of the vessel. It should be understood that the size of the bladder may change as directed.

The exemplary embodiment of FIG. 3 uses a metal vessel 40. The exemplary embodiment of FIG. 10 uses a plastic vessel 140. As explained in more detail below, FIG. 10 also illustrates an embodiment in which the vessel containing the refrigerant collapses under pressure from a bladder containing pressurizing fluid pushing in on the vessel. Plastic vessel 140 may also be used with an internal bladder such as in FIG. 3. Plastic containers such as one and two liter corbonated soft drink bottles are accetable int he present invention even though the system is designed to operate under relatively high pressures, approximately 52 psi (360 kPa), at normal temper and may be exposed to elevated temperatures. Plastic vessels are manufactured inexpensively and at relatively low cost. They have a center section 142 which has a relatively thin cylindrical wall 148 and a bottom end 144 and an open neck end 146 which have somewhat thicker walls for added strength. Ends 144 and 146 are bonded to the ends of center section 142 during manufacture. Because the diameter of the center section 142 is relatively small, the stress on cylindrical wall 148 is well within tolerances of hte plastic material. The stress on wall 148 is calculated using the following formula:

$$S = Pr/T$$

where S is stress on wall 148 (FIG. 10), P is the internal pressure (approximately 52 psi at standard temperature), r is the radius and T is the wall thickness. Carbonated soft drinks are stored at reasonably high pressure. Commercially available bottles are strong enough to hold the fluids used in the present invention without bursting at substantially above 52 psi pressure. The vessel must be dieigned for higher pressures because the closed vessel may be subjected to elevated temperatures, which will increase the internal pressure.

The material of wall 148 may be subjected to creep, slow movement of the wall in response to pressure. Creep is inversely proportional to the modulus of elasticity of the material. If the vessel is filled and used promptly, creep does not cause major problems, but the vessel is designed for relatively long shelf life in a filled condition, so that creep may be a factor. Creep adversely influences the pressure vesel because it causes an expansion of wall 148, which increases the radius of the cylindrical wall and decreases the thickness. Both result in increased stress to the vessel.

Creep can be avoided by using a winding of a high modulus of elasticity material such as Keviar arimid fiber. As shown in FIG. 10, a strand of fiber 150 is laid longitudinally from the bottom of vessel 140 along the outside wall 148 of the center section 412. Strand 150 is wound in a helix 152 around the outside of wall 148 beginning near the top of vessel 140. The helix extends toward the bottom, but it is not entirely shown in FIG. 10. Each winding covers a portion of the initial fiber that extends longitudinally along the center secition 142. The end of the last wind appears at 154. It is tied to an extension from the longitudinal portion, and the entire winding is secured. Adhesives may also secure the windings. Depending on the material chosen for the walls of vessel 140, the pitch of helical windings 152 can be modified to minimize the effect of creep.

Rather than having the bladder expanding within vessel 40, if the walls of the vessel are flexible, the pressure from the pressurizing fluid can also be used to collapse the vessel to decrease its internal volume. FIG. 10 shows an embodiment utilizing that principle in which plastic bottle 140 is the vessel that carries the refrigerant. Cap 160 seals vessel 140, and an outlet tube 165 sealed by valve 167 permits the liquid refrigerant to flow out of vessel 140 for use. The plastic material that forms vessel 140 withstands pressure but allows the container to be collapsed when external forces are applied to the container. The plastic material is tough and resists uneven applications of force.

In the exemplary embodiment of FIG. 10, vessel 140 is mounted within an outer container or sleeve 170. The sleeve is not sealed at its top and acts only to surround vessel 140. It may be formed of rigid material or may be a bag-like member formed of relatively high tensile strength fgabric to resist force pushing outward on it.

A bladder 175 extends the length and at least partially around vesel 140 (FIG. 10). Bladder 175 may actually encompass the entire first container if desired. Clamp 177 seals bladder 175. One pours pressurizing liquid into the bladder when the clamp is temporarily removed. Alternatively, bladder 175 can be permanently sealed but be provided with a valved inlet opening. As liquid refrigerant is drawn from vessel 140, the pressurizing liquid in bladder 175 pushes against the outside walls of the vessel causing the walls to collapse, and the volume within the vessel to decrease. This action maintains the 52 psi pressure on the refrigerant within vessel 140 so that the refrigerant stays as a liquid.

The pressurizing fluid in bladder 90 vaporizes, which causes the bladder to expand. The higher 52 psi pressure on the bladder walls displaces the gas-filled portion of the space in vessel 40 until all of the space within the outer container is liquid refrigerant or bladder 90.

Various modifications and changes may be made in the configuration described above that come within the spirit of this invention. The invention embraces all such changes and modifications coming within the scope of the appended claims.

I claim:

1. A container for storing and dispensing a refrigerant at a pressure above its vapor pressure, the container comprising:
    a. a vessel for containing the refrigerant;
    b. a expandable container mounted within the vessel and holding a second fluid, the expandable container positioned to exert force on the refrigerant in the vessel, the second fluid having a vapor pressure greater than the vapor pressure of the refrigerant in the first container, the expandable container having at least one flexible wall for acting on the refrigerant for pressurizing the refrigerant;
    c. wherein the expandable container is formed of a flexible material, the expandable container comprising a sleeve extending at least partially along the outside wall of the expandable container.

2. The container of claim 1, further comprising channeling means in the sleeve for channeling fluid from one part of the vessel to another part of the vessel when the expandable container expands against the inside wall of the vessel.

3. A dispenser for dispensing pressurized refrigerant at a pressure above its normal vapor pressure comprising:
    a. a vessel being capable of holding refrigerant and closure means for closing the vessel;
    b. pressurizing means associated with the vessel for acting on the refrigerant to pressurize the refrigerant above its vapor pressure, the pressurizing means comprising bladder means formed of a flexible material for receiving a second fluid, which has a vapor pressure higher than the vapor pressure of the refrigerant, the pressure of the second fluid in the bladder means acting on the outside of the bladder means, and the outside of the bladder means acting on the refrigerant to minimize the volume of the refrigerant in the vessel to pressurize the refrigerant within the vessel; and
    c. wherein the bladder further comprises a sleeve at least partially along the outside wall of the bladder.

4. The container of claim 3, further comprising channeling means in the sleeve for channeling fluid from one part of the vessel to another part of the vessel when the bladder means expands against the inside wall of the vessel.

5. The pressurized dispenser of claim 4 wherein the channeling means is formed of material that is more rigid than the material of the bladder means, the channeling means having at least two longitudinal channels extending parallel to each other, the end of one channel being longitudinally spaced from the end of the other channel.

* * * * *